US008409793B2

(12) United States Patent
Perrut et al.

(10) Patent No.: US 8,409,793 B2
(45) Date of Patent: Apr. 2, 2013

(54) METHOD FOR PREPARING A SAMPLE (75) Inventors: Michel Perrut, Nancy (FR); Frédéric Imbs, Velines (FR); Frantz Deschamps, Nancy (FR)

(73) Assignee: Histolex, Martillac (FR)

( * ) Notice: Subject to any disclaimer, the term of this patent is extended or adjusted under 35 U.S.C. 154(b) by 223 days.

(21) Appl. No.: 12/094,158

(22) PCT Filed: Sep. 20, 2006

(86) PCT No.: PCT/FR2006/002149
§ 371 (c)(1),
(2), (4) Date: Sep. 25, 2008

(87) PCT Pub. No.: WO2007/034071
PCT Pub. Date: Mar. 29, 2007

(65) Prior Publication Data
US 2009/0203066 A1  Aug. 13, 2009

(30) Foreign Application Priority Data

Sep. 21, 2005  (FR) ..................... 05 09635

(51) Int. Cl.
*A01N 1/00* (2006.01)
(52) U.S. Cl. ........................... 435/1.1; 435/1.2; 435/366
(58) Field of Classification Search .......................... None
See application file for complete search history.

(56) References Cited

U.S. PATENT DOCUMENTS
2003/0072677 A1 *  4/2003  Kafesjian et al. ............... 422/33

FOREIGN PATENT DOCUMENTS
WO   WO 2005/001437    *  1/2005
WO   WO 2005001437        1/2005

OTHER PUBLICATIONS

Lefurgey et al, 1999. Biomedical Applications of Microprobe Analysis. Chapter 2—Preparatory techniques, including cryotechnology. pp. 59-85.*
Papaconstantinou et al, 2991. Effect of B-estradiol and Bisphenol A on heat hock protein levels and localization in the mouse uterus are antagonized by the antiestrogen ICI 182,780. Toxicological Sciences, vol. 63:173-180.*

* cited by examiner

*Primary Examiner* — Blaine Lankford, Jr.
(74) *Attorney, Agent, or Firm* — Young & Thompson (57) ABSTRACT A method for preparing a sample consisting of biological tissue in a solid matrix includes steps of: contacting the sample with a first compressed fluid stream wherein the matrix is soluble so as to extract the solid matrix, contacting the sample with a second compressed fluid, adapted to impregnate the tissue with an aqueous or water-soluble substance, evacuating the second compressed fluid gradually and in controlled manner, recovering the sample.

11 Claims, 4 Drawing Sheets

METHOD FOR PREPARING A SAMPLE

FIELD OF THE INVENTION

The present invention lies in the field of histology and relates more particularly to a method for preparing a sample.

BACKGROUND OF THE INVENTION

Histology is the microscopic study of the morphology and the composition of biological tissues. This study is of utmost importance, in particular for the purpose of establishing a diagnosis which makes it possible to orient the treatment of a patient. Prior to their microscopic study, biological tissues are usually embedded in a matrix which is in the solid state at room temperature, and then prepared in the form of thin sections having a thickness of the order of a few micrometers, and finally subjected to staining reactions allowing the identification of the various constituents of the tissue.

The reference methods in the field of preparation of biological tissues intended for microscopic examination have been described for many years, for example in the book by M. Langeron "Précis de microscopic" Ed. Masson and Co., Paris 1942 or that by P. Ganter and G. Jollès, "Histochimie normale et pathologique" Ed. Gauthier-Villars, Paris 1969. The embedding is designed to allow the preparation of thin and regular sections from the piece of tissue to be examined. The most widely used embedding medium is paraffin. Paraffin being hydrophobic, the sample should be subjected to dehydration, usually by immersing in baths of ethanol of increasing strength, and then in toluene or xylene baths. The sample is then placed in a bath containing molten paraffin, which then infiltrates the entire piece, this phase is known by the name impregnation. The piece is then molded in order to lead, after cooling, to a solid paraffin block within which the biological piece is embedded. The sections of the paraffin block are then prepared with a microtome which makes it possible to produce thin sections, generally 1 to 3 µm thick.

These sections are collected on glass slides and are stained. As the stains are often water-soluble, the sections must be rehydrated before staining so that they are in a state which makes them capable of undergoing the histological stainings. The rehydration is performed by paraffin removal from the sections, which is carried out by immersion in toluene or xylene baths, and then by immersion in baths of alcohol of decreasing strength, and then in water.

The preparation of these sections before staining (paraffin removal and hydration) uses large quantities of organic solvents, particularly alcohols, toluene or xylene. This results in a high cost because of the regulatory constraints regarding the use, and then the disposal or recycling, of such solvents.

It is also known that trends in the uses and regulations lead to the use of organic solvents being reduced or even stopped. By analogy with certain solvents, such as benzene or chloroform, which were customarily handled over the past decades and whose use is now severely regulated, it can be feared that the handling of solvents such as toluene or xylene will in future be subjected to extremely severe regulatory constraints.

A need therefore exists for novel methods for preparing samples for medical analysis with a view to reducing or eliminating the use of organic solvents.

BRIEF SUMMARY OF THE INVENTION

The aim of the present invention is to provide a method for treating biological tissues embedded in a solid matrix, particularly thin sections of dehydrated tissues embedded in paraffin, in order to produce tissues free of this matrix and to bring them to a physicochemical state, in particular a state of hydration or impregnation with a water-soluble substance, which makes them suitable for being subjected to histological stainings.

DETAILED DESCRIPTION OF THE INVENTION

Examples of organic solvents, in the pure state or in the form of a mixture, are known whose use has been evaluated in the field of the preparation of a sample for histological analysis, and which are suitable for replacing toluene or xylene. There may be mentioned in particular dioxane, chloroform, methylcyclohexane or aliphatic hydrocarbons. It is well known that these solvents pose problems of toxicity and/or problems of safety during handling because of their inflammable character. Moreover, persons skilled in the art know that the quality of the samples treated using these solvents is quite often lower than that obtained with the reference method using toluene.

Compressed fluids, particularly liquid or supercritical carbon dioxide, are used in an increasing number of applications for numerous methods where they make it possible to advantageously replace organic solvents.

An overview of the various states of a fluid and its properties in each of these states will first of all be given. It is known that substances are generally known in three states, namely solid, liquid or gaseous and that it is possible to pass from one state to another by varying the temperature and/or the pressure. In addition to the solid state, the liquid state and the gaseous state exist which are separated by the vaporization/condensation curve; and a point exists beyond which it is possible to pass from the liquid state to the gaseous or vapor state without boiling taking place or, conversely, without condensation taking place, this being continually: this point is called the critical point.

A supercritical fluid is characterized either by a pressure and temperature which are greater than the critical pressure and temperature, respectively, in the case of a pure substance, or by a representative point (pressure, temperature) situated outside the envelope of critical points represented on a diagram (pressure, temperature) in the case of a mixture; it thereby exhibits, for very many substances, a high solvent power that bears no comparison with that observed in this same fluid in the compressed gas state. The same applies to the so-called "subcritical" liquids, that is to say liquids which exist in a state characterized either by a pressure greater than the critical pressure and by a temperature less than the critical temperature in the case of a pure substance, or by a pressure greater than the critical pressures and by a temperature less than the critical temperatures of the components in the case of a mixture (see in this regard the article by Michel PERRUT-Les Techniques de l'Ingéenieur "Extraction par fluide supercritique, J 2 770-1 to 12, 1999"). The large and modulable variations in the solvent power of supercritical fluids are moreover used in numerous methods of extraction (solid/fluid), fractionation (liquid/fluid), analytical or preparative chromatography, treatment of materials (ceramic and polymer materials, and the like) and generation of particles. Chemical or biochemical reactions are also carried out in such solvents.

It should be noted that the physicochemical properties of carbon dioxide and its critical parameters (critical pressure: 7.4 MPa and critical temperature: 31° C.) make it the preferred solvent in numerous applications, especially since it exhibits no toxicity and is available at very low cost in very large quantities. Other fluids may also be used under similar conditions, such as nitrous oxide, light hydrocarbons having two to four carbon atoms, ethers and certain halogenated hydrocarbons.

It should be noted that water is in general only very slightly soluble in fluids at supercritical pressure and liquefied gases conventionally used, and in particular in carbon dioxide under high pressure in which water is only soluble in an amount of 1 to 3 g/kg between 25 and 50° C. However, although low, this solubility causes great consequences on the properties of the fluid thus hydrated, and also results in the dehydration of the material treated with this fluid when the latter is introduced without containing water.

In the text which follows, and for the sake of simplicity, compressed fluid will mean any fluid brought to a pressure substantially greater than atmospheric pressure. Fluid at supercritical pressure will mean a fluid brought to a pressure greater than its critical pressure, that is to say either a supercritical fluid proper, or a so-called subcritical liquid as defined above. Likewise, liquefied gas will mean a liquid, consisting of a compound which is in the gaseous state at atmospheric pressure and at room temperature, brought to a pressure and to a temperature below its critical pressure and temperature, respectively.

It is known that numerous methods of extraction using compressed fluids, particularly carbon dioxide at supercritical pressure, have been developed and currently have industrial applications (see in this respect the article by Michel PERRUT mentioned above). These methods are based on bringing a material containing the substance to be extracted into contact with a compressed fluid, under temperature and pressure conditions for which the compressed fluid can solubilize the substance to be extracted. Persons skilled in the art know that the structure of this material may be altered during the implementation of such a method of extraction. The dissolution of part of the compressed fluid inside the material, followed by the decompression which accompanies a rapid desorption of the compressed fluid, can irreversibly modify the structure of this material.

In addition, at the end of the extraction with the compressed fluid, particularly with liquid or supercritical carbon dioxide, the material becomes dehydrated. Moreover, it is well known that numerous hydrocarbons, especially paraffin, have a sufficiently high solubility in liquid or supercritical carbon dioxide for it to be possible to carry out such extraction methods intended to recover said hydrocarbons. However, it is easily understood that the use of such extraction methods could seriously impair the structure of a biological tissue embedded in a solid matrix, which would seriously degrade the quality of the results of a microscopic study and of the diagnosis resulting therefrom. In addition, after the extraction of the paraffin with compressed carbon dioxide, the biological tissue would become dehydrated, which would not make it possible to carry out histological stainings using hydrophilic stains.

The advantageous properties of compressed fluids for carrying out methods of extracting a substance from a material make it possible, conversely, to obtain the impregnation of a material. Methods of impregnation using compressed fluids, particularly carbon dioxide at supercritical pressure, are indeed known in which a substance solubilized or dispersed in the compressed fluid impregnates a solid matrix, as described in patent FR 2 798 863. These methods take advantage of both the favorable diffusion properties of compressed fluids and the interactions between the compressed fluid and the solid matrix which leads to a modification of the structure of this matrix, thus making it capable of being impregnated with a substance. These methods are being increasingly developed, particularly for the treatment of polymers, as described in a recent review by D. L. TOMASKO et al. ("A review of $CO_2$ applications in the Processing of Polymers" published in Industrial & Engineering Chemistry Research, volume 42, p. 6431 to 6456, 2003). Recent patents and publications teach that the use of these impregnation methods causes, in general, impairment of the microstructure of the matrix to be impregnated. Numerous examples are thus known in which the impregnation of a solid matrix with the aid of a compressed fluid is unavoidably accompanied by the formation of a porous structure, such as expanded foams or microporous pieces.

A method of preparing biological samples for histological analysis, using supercritical fluids, is also known from patent application WO 2005/001437. This method is intended for embedding biological tissues in a solid matrix, preferably consisting of paraffin. According to this application, the biological sample is brought into contact with a composition comprising a supercritical fluid, and is then impregnated by bringing into contact with the molten embedding matrix.

The aim of the present invention, for its part, is to provide a method which makes it possible to extract and remove the solid matrix, particularly paraffin, from a biological tissue embedded in this matrix, and to bring this tissue to a hydrated state, or to a state impregnated with a water-soluble substance, which state makes it capable of undergoing histological stainings, without any damaging impairment of the structure of this tissue.

The subject of the present invention is thus a method for treating a sample consisting of a biological tissue embedded in a solid support matrix, characterized in that it comprises the successive steps consisting in:

bringing the sample into contact with a stream of a first compressed fluid in which said support matrix is soluble, so as to cause the extraction of said solid matrix, bringing the sample into contact with a second compressed fluid, capable of impregnating the tissue by an aqueous or water-soluble substance, evacuating the second compressed fluid gradually and in a controlled manner, recovering the sample.

The method which is the subject of the invention is particularly advantageous in that it makes it possible to eliminate the use of toxic organic solvents, particularly toluene or xylene, during the preparation of a biological sample for a microscopic study.

Moreover, the method which is the subject of the invention requires handling the sample only during its introduction into a reactor at high pressure and during its recovery in this reactor. It is therefore particularly advantageous in that it makes it possible to simplify the complex preliminary treatments comprising multiple handling steps, in particular successive immersions of the sample in organic solvent baths.

This invention is based on the fact that it is surprising to observe that bringing a biological tissue embedded in a solid matrix into contact with a first compressed fluid in which said matrix is soluble, so as to extract the embedding matrix, and then with a second compressed fluid in which an aqueous or water-soluble substance is solubilized or dispersed makes it possible, after a gradual and controlled decompression, to prepare a tissue whose structure is not impaired and which becomes impregnated with said aqueous or water-soluble substance, which makes it capable of undergoing histological stainings. Unlike the methods of extraction or impregnation with the abovementioned compressed fluids, the method which is the subject of the invention uses compressed fluid compositions, temperature and pressure conditions, and a gradual and controlled decompression step which do not cause impairment of the structure of the biological tissue. It is in addition surprising to observe that some compositions of the two compressed fluids make it possible gradually to extract the hydrophobic embedding matrix and to impregnate the tissue with an aqueous or water-soluble substance.

The use of a second compressed fluid which comprises carbon dioxide and a water-soluble organic solvent, as well as, in a specific embodiment, a water-soluble aqueous solvent, makes it possible to bring the tissue to a controlled physicochemical state compatible with the requirements of stainings customarily performed for histological analysis.

According to one embodiment of the invention, the first compressed fluid comprises carbon dioxide at supercritical pressure and optionally an organic solvent. Preferably, the organic solvent comprises an alcohol having 1 to 5 carbon atoms, and in particular 2 carbon atoms.

In another variant of this embodiment of the invention, it is possible to use, as first compressed fluid, a mixture of carbon dioxide, water-soluble organic solvent and aqueous solvent.

According to the invention, the second compressed fluid advantageously comprises a mixture of carbon dioxide and a water-soluble organic solvent, optionally supplemented with an aqueous solvent.

According to another particularly advantageous embodiment of the invention, the first and second compressed fluids are identical.

In an advantageous embodiment, the first and second compressed fluids are maintained, during the bringing into contact with the samples, at a pressure between 4 and 70 MPa, preferably at a pressure between 6 and 30 MPa, and at a temperature between 0 and 50° C., preferably between 20 and 40° C.

Other compounds may be added to each of the two compressed fluids, particularly in order to improve the quality of the tissue after treatment and to ensure its good preservation, to reduce the treatment period, to impregnate the tissue with a reagent intended to perform, prepare or modify the stainings, or alternatively to control the pH of the compressed fluid comprising an aqueous solvent.

Depending on the compositions of the two compressed fluids and the parameters for the method, the steps of extraction of the embedding matrix and of impregnation of the tissue with an aqueous substance may be advantageously performed either concomitantly or successively.

The method which is the subject of the invention is particularly advantageous in that it makes it possible to prepare a biological tissue intended for histological analysis using moderate operating conditions, in particular a temperature close to room temperature. The method which is the subject of the invention is therefore particularly suitable for the preparation of biological tissues for performing immunohistochemistry, lectinohistochemistry, histoenzymology or alternatively in situ hybridization techniques.

The biological tissue is preferably cut in the form of a thin section, advantageously having a thickness between 1 and 5 μm.

The method which is the subject of the invention is advantageous when it is applied to micrometric sections of tissues embedded in paraffin, and particularly when said sections are mounted on a glass slide.

The method which is the subject of the invention makes it possible to treat samples of biological tissues of human, animal or plant origin, among which there may be mentioned epithelia, particularly covering epithelia and glandular epithelia; connective tissue, particularly loose connective tissues, dense connective tissues, bone tissues, cartilaginous tissues, lymphatic and hematopoietic tissues; nerve tissues, particularly the tissues of the central nervous system and of the peripheral nervous system; muscle tissues, particularly smooth, striated skeletal or striated cardiac muscle tissues.

Among the stainings to which the samples treated by the method which is the subject of the invention may be subjected, there may be mentioned bichromic staining, particularly staining with hemalun-eosin, hemalun-phloxin, hemalun-erythrosine; trichromic staining, particularly staining with hemalun-eosin-saffron, hemalun-phloxin-saffron, Masson's trichromic staining with light green or with aniline blue; panoptic staining, particularly May-Grnüwald Giemsa staining; special stainings, particularly staining with periodic acid-Schiff, staining with Sudan black, staining with orcein, Perls staining; immunohistochemical staining, particularly for the identification of tumor antigens. It is also possible to mention the sample preparation procedures used in the field of lectinohistochemistry, histoenzymology or in situ hybridization.

Figure 1:
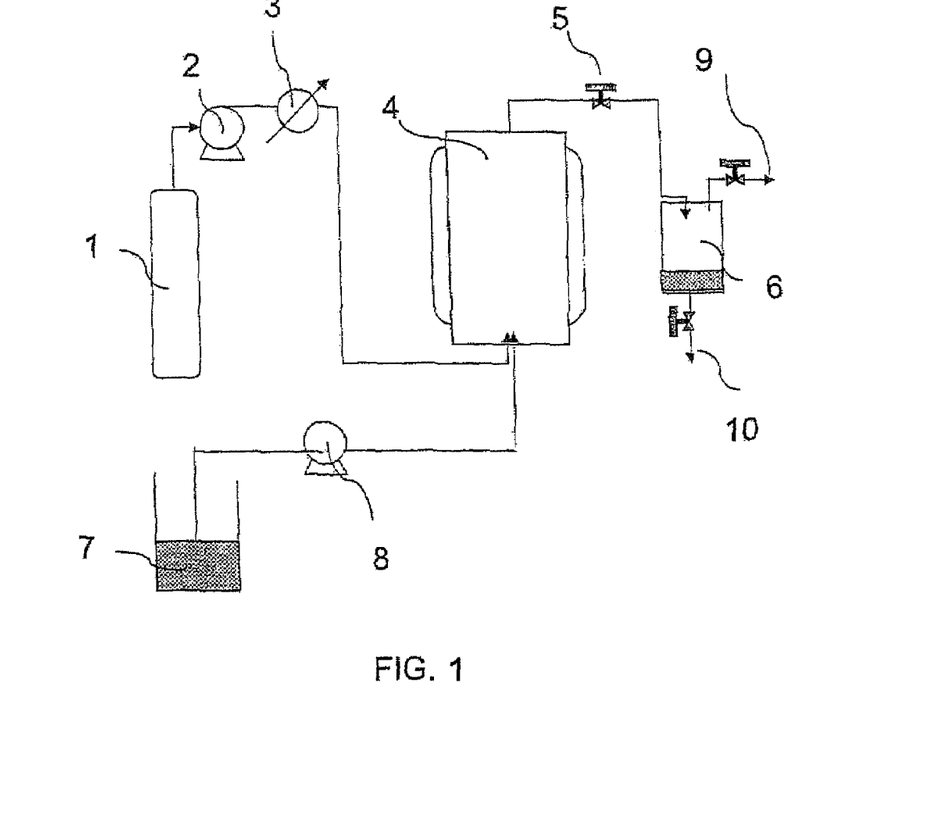
FIG. 1 represents a diagram of an equipment which makes it possible to carry out the method which is the subject of the invention.

The various implementation examples presented in order to illustrate without limitation the method according to the invention were carried out in an equipment in conformity with that described below.

The latter comprises a reserve 1 of a liquefied gas, consisting of carbon dioxide, whose outlet is connected, by a pump 2 and an exchanger 3, which make it possible to bring the gas stream passing though them to the desired pressure and temperature, respectively, to an autoclave 4. This autoclave is provided with means, not represented in the drawing, which make it possible to receive the glass slides supporting the thin sections, and to flush them with the carbon dioxide stream from the reserve 1.

The autoclave 1 comprises withdrawing means consisting of a pressure regulating device 5 which is connected to a separator 6 in which it is brought to the gaseous state before being discharged into a vent 9.

The equipment also comprises a line for adding solvent comprising a reservoir 7 connected to the autoclave 4 by a pump 8, which makes it possible to admit therein an organic or aqueous solvent as well as other compounds capable of being mixed with the solvent. It will be possible to recover these various components in the liquid state at the bottom 10 of the separator 6.

Example 1

Treatment of Thin Sections of Seminal Vesicle

In this example, glass slides, on which there have been deposited thin sections of seminal vesicle having a thickness of between 1 and 5 μm embedded in paraffin, are introduced into the autoclave 4. The latter was then closed and its temperature set at 35° C. The following steps of the method were carried out:
  a) the autoclave was flushed with a carbon dioxide stream introduced with the aid of the pump 2 at a pressure of 20

MPa, at a temperature of 35° C. and at a flow rate of 4 kg/h. This flushing was maintained for 30 minutes,
b) the autoclave was then flushed with a stream of a mixture composed of 75% by mass of carbon dioxide, 22.5% of ethanol and 2.5% of water, provided by the pumps 2 and 8 at a pressure of 20 MPa, at a temperature of 35° C. and at a flow rate of 4 kg/h. This flushing was maintained for 15 minutes,
c) the pumping of the compressed fluid was stopped, and the pressure was gradually reduced in the autoclave down to atmospheric pressure, while maintaining the temperature at 35° C. The duration of this decompression was 30 minutes,
d) the autoclave was opened as soon as it reached atmospheric pressure, and the glass slides were recovered.

It was possible to note that the appearance of each of the glass slides was identical. No trace of paraffin was observed during a microscopic study of these slides. The slides were then subjected to a staining procedure. Masson's trichromic staining was used (light green variant) which combines a nuclear staining with hemalun, a cytoplasmic staining with a mixture of acid stains (Fuchsin-Ponceau) and an "elective" staining of collagen with another acid stain, light green. The staining was carried out using the kit "Trichrome de Masson variante au vert lumière—code 361350-0000" (Masson's trichrome kit, variant with light green—code 361350-000) marketed by the company Réactifs R. A. L. following the procedure consisting in staining the slides in Mayer's hemalun for 10 minutes; rinsing in water; staining in the Fuchsin-Ponceau solution for 5 minutes; rinsing in water; mordanting in a phosphomolybdic acid bath for 3 minutes; without rinsing, staining in the solution of light green for 5 minutes; rinsing in 2 baths of 1% acetic water; successively differentiating in baths of alcohol of increasing strength; transferring to a toluene bath and finally mounting the slides.

Once stained, the slides were examined in white light, with the aid of a microscope using ×20 and ×40 lenses. As a reference, thin sections obtained from the same tissue were freed of paraffin and then hydrated by the reference method (immersion in baths of toluene and then of ethanol of decreasing strength, and then of water) before undergoing identical staining.

Figure 2:
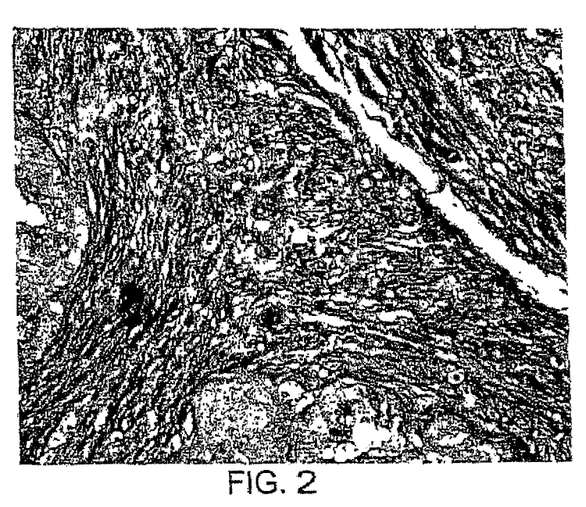
FIGS. 2 and 4 represent photographs obtained during the microscopic examination of a section of seminal vesicle treated according to the method which is the subject of the invention as described in example 1.
Figure 3:
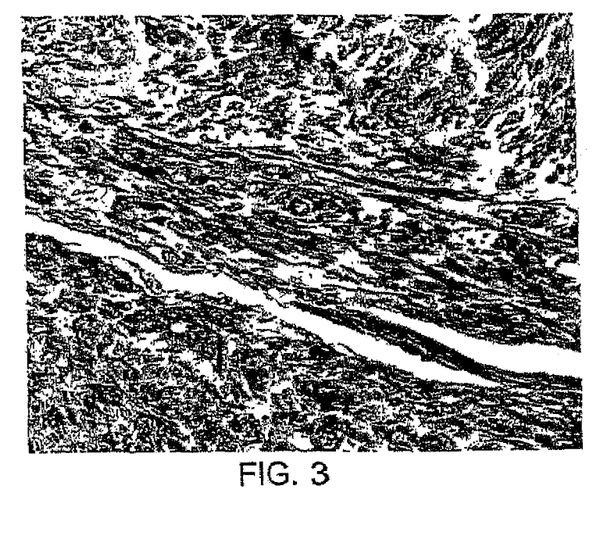
FIGS. 3 and 5 represent photographs obtained during the microscopic examination of a section of seminal vesicle treated according to the conventional reference method as described in example 1.
Figure 4:
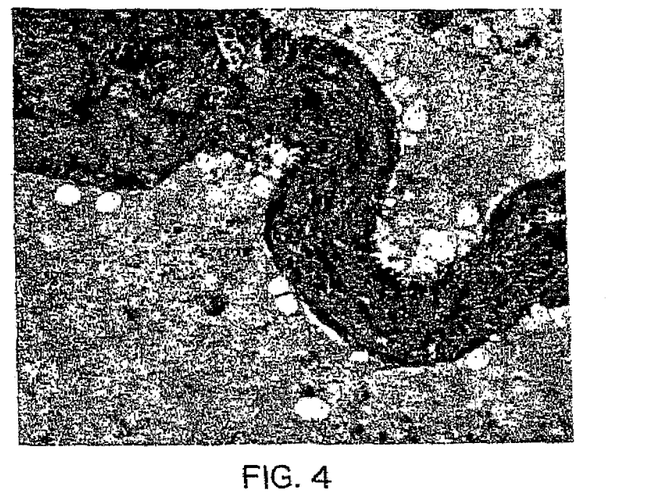
Figure 5:
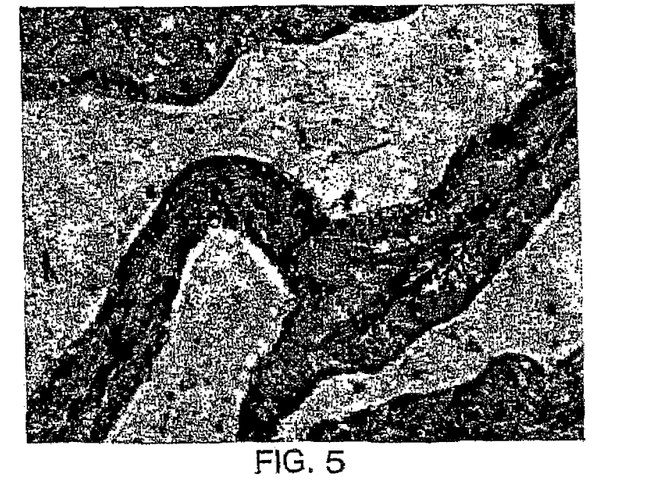
Figure 6:
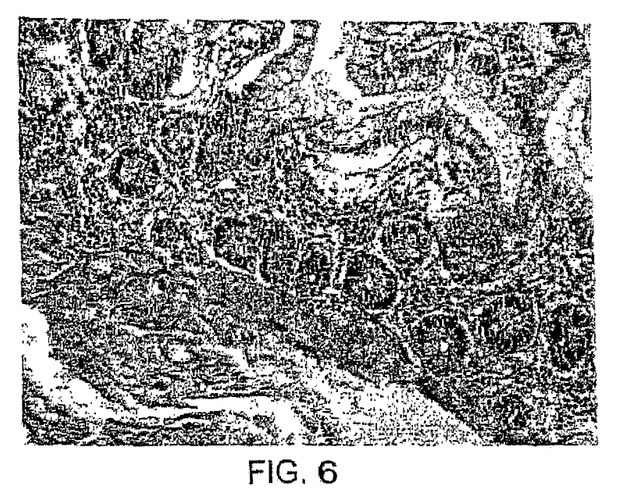
Figure 7:
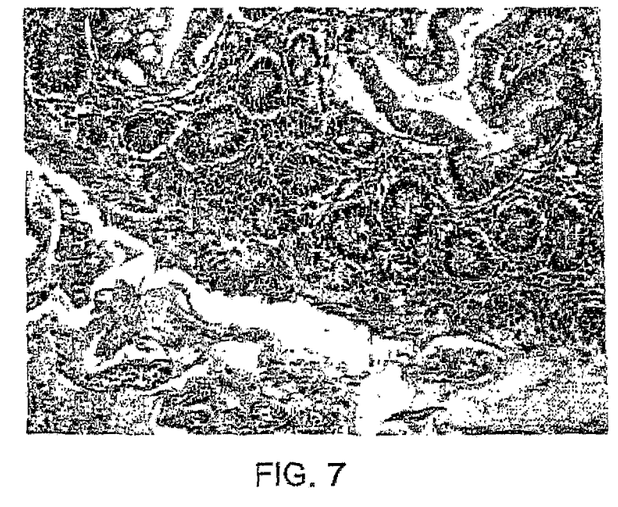

After staining, the appearance of the slides treated by the method which is the subject of the invention (FIGS. 2 and 4) proved to be identical to that of the reference slides (FIGS. 3 and 5). No tissue impairment was observed and the histological components were well preserved with a characteristic chromatin. The staining made it possible to distinguish in both cases, in green, inside the lumens, the seminal secretion. The contour of the lumens consists of the epithelial covering, stained in red, whose cells, which are poorly arranged, are characteristic of the seminal vesicle. The hyalin material consisting of amyloid deposits was stained pink. The cell nuclei appeared stained violet blue including a few spermatozoa. The red blood cells are stained bright red. The smooth muscle appeared dark red, at the periphery and inside the vesicle. Finally, the entire topography of the section was clearly recognized. The tissue was therefore in a physicochemical state, in particular in a hydration state, allowing it to successfully undergo a staining procedure.

The method which is the subject of the invention is therefore a method that is capable of replacing the reference methods, and makes it possible to obtain an equivalent sample quality, without the use of toxic organic solvents.

Example 2

Variant of the Application of the Method which is the Subject of the Invention

This example illustrates one particularly simple embodiment of the method which is the subject of the invention where, after extraction of the paraffin with pure carbon dioxide, a defined volume of aqueous or hydrophilic substance(s), such as for example a mixture of ethanol and water, was introduced at the bottom of the autoclave 4. The tissue was then left in contact with the fluid thus saturated with ethanol and with water.

The glass slides, on which thin sections of seminal vesicle embedded in the paraffin were deposited, were introduced into the autoclave 4 and maintained in its top section with the aid of a support not represented in the drawing. The autoclave was closed, and its temperature set at 35° C. The following steps of the method were carried out:
a) the autoclave was flushed with a carbon dioxide stream introduced with the aid of the pump 2 at a pressure of 20 MPa, at a temperature of 35° C. and at a flow rate of 4 kg/h. This flushing was maintained for 30 minutes,
b) the pumping of the compressed fluid was then stopped and 50 ml of an ethanol/water mixture 1/1 v/v were introduced into the bottom section of the autoclave 4 by means of the pump 8, and the pressure was maintained at 20 MPa with the aid of the pressure regulating valve 5 allowing the fluid to escape from the autoclave. The sample was left for 15 minutes in contact with the second compressed fluid consisting of carbon dioxide, in which ethanol and water were dissolved,
c) the pressure was gradually reduced in the autoclave until it is brought to atmospheric pressure, while maintaining the temperature at 35° C., the duration of this decompression being 30 minutes,
d) the autoclave was opened as soon as it returned to atmospheric pressure, and the glass slides were recovered.

After Masson's trichromic staining, according to a protocol identical to that of example 1, including the simultaneous staining of a reference slide after removal of paraffin by immersion in toluene baths, it was observed that the microscopic appearance of the slide treated according to the method which is the subject of the invention was identical to that of the reference slide.

Example 3

Treatment with the Aid of Liquid Carbon Dioxide

A thin section of the small intestine was subjected to a treatment identical to that described in example 2, with the exception of the temperature of the autoclave and of that of the fluid which were maintained at 25° C. and of the pressure in the autoclave which was set at 8 MPa. The carbon dioxide was therefore in the liquid state. Moreover, the duration of step a) (extraction of the paraffin) was brought to 180 minutes.

After hemalun-eosin-saffron staining including the simultaneous staining of a reference slide after paraffin removal by immersion in toluene baths, it was observed that the appearance of the slide treated according to the method which is the subject of the invention was identical to that of the reference slide. In both cases, the chromatin is characteristic, and the histological components are well preserved and differentiated.

The invention claimed is:

1. A method for treating a sample consisting of a biological tissue embedded in paraffin, the method comprising:

bringing the sample into contact with a stream of a first compressed fluid to extract the paraffin, said first compressed fluid selected from liquid or supercritical carbon dioxide having a pressure between 4-70 MPa and a temperature between 0-50° C.;

bringing the sample into contact with a second compressed fluid to impregnate the tissue to bring the tissue to a hydrated state, or to a state impregnated with a water-soluble substance, each of said states making the tissue capable of undergoing histological staining, without any damaging impairment of a structure of the tissue, said second compressed fluid comprising a mixture of carbon dioxide, water and a water-soluble organic solvent, said second compressed fluid having a pressure between 4-70 MPa and a temperature between 0-50° C.;

evacuating the second compressed fluid gradually and in a controlled manner; and recovering the sample.

2. The method as claimed in claim 1, wherein the first compressed fluid additionally comprises an organic solvent.

3. The method as claimed in claim 2, wherein the organic solvent comprises an alcohol having between 1 and 5 carbon atoms.

4. The method as claimed in claim 1, wherein the first and second compressed fluids are identical.

5. The method as claimed in claim 1, wherein during the bringing the sample into contact steps, the first and second compressed fluids are maintained at a pressure between 6-30 MPa, and at a temperature between 20-40° C.

6. The method as claimed in claim 1, wherein the extraction of the paraffin and the impregnation of the tissue are performed concomitantly.

7. The method as claimed in claim 1, wherein the biological tissue is cut in the form of a thin section.

8. The method as claimed in claim 7, wherein the thin section of biological tissue is placed on a glass slide.

9. The method as claimed in claim 1, wherein the water-soluble organic solvent is ethanol.

10. The method as claimed in claim 3, wherein the organic solvent comprises an alcohol having 2 carbon atoms.

11. The method as claimed in claim 7, wherein the thin section has a thickness between 1-5 μm.

* * * * *

UNITED STATES PATENT AND TRADEMARK OFFICE
CERTIFICATE OF CORRECTION

PATENT NO.        : 8,409,793 B2
APPLICATION NO.   : 12/094158
DATED             : April 2, 2013
INVENTOR(S)       : Perrut et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this
First Day of September, 2015

Michelle K. Lee
*Director of the United States Patent and Trademark Office*